(12) United States Patent
Jacky et al.

(10) Patent No.: US 10,697,002 B2
(45) Date of Patent: Jun. 30, 2020

(54) AMPLIFICATION AND DETECTION OF NUCLEIC ACIDS IN A BIOLOGICAL SAMPLE

(71) Applicant: Quest Diagnostics Investments Incorporated, Wilmington, DE (US)

(72) Inventors: Lucien Jacky, Orange, CA (US); Albert Castro, Walnut, CA (US); Peter Lee, Tustin, CA (US); Jose Matud, Long Beach, CA (US); Michelle Tabb, Santa Ana, CA (US)

(73) Assignee: Quest Diagnostics Investments Incorporated, Wilmington, DE (US)

( * ) Notice: Subject to any disclaimer, the term of this patent is extended or adjusted under 35 U.S.C. 154(b) by 277 days.

(21) Appl. No.: 15/529,343

(22) PCT Filed: Nov. 24, 2015

(86) PCT No.: PCT/US2015/062376
§ 371 (c)(1),
(2) Date: May 24, 2017

(87) PCT Pub. No.: WO2016/085955
PCT Pub. Date: Jun. 2, 2016

(65) Prior Publication Data
US 2017/0268043 A1  Sep. 21, 2017

Related U.S. Application Data

(60) Provisional application No. 62/084,257, filed on Nov. 25, 2014.

(51) Int. Cl.
| C12Q 1/6806 | (2018.01) |
| C12Q 1/6848 | (2018.01) |
| C12Q 1/6853 | (2018.01) |
| C12Q 1/686  | (2018.01) |
| C12N 1/06   | (2006.01) |
| C12N 15/10  | (2006.01) |

(52) U.S. Cl.
CPC ............. *C12Q 1/6806* (2013.01); *C12N 1/06* (2013.01); *C12N 15/1003* (2013.01); *C12Q 1/686* (2013.01); *C12Q 1/6848* (2013.01); *C12Q 1/6853* (2013.01); *C12Q 2523/32* (2013.01); *C12Q 2565/629* (2013.01); *Y02A 50/53* (2018.01)

(58) Field of Classification Search
None
See application file for complete search history.

(56) References Cited

U.S. PATENT DOCUMENTS

| 2003/0082563 A1 | 5/2003  | Bell et al. |
| 2009/0018323 A1 | 1/2009  | Erbacher et al. |
| 2009/0117557 A1 | 5/2009  | Wang et al. |
| 2011/0207140 A1 | 8/2011  | Handique et al. |
| 2012/0293796 A1 | 11/2012 | Ludowise et al. |
| 2013/0029338 A1 | 1/2013  | Jovanovich et al. |
| 2014/0134631 A1 | 5/2014  | Clime et al. |

OTHER PUBLICATIONS

Manage et al., "On-chip PCR amplification of genomic and viral templates in unprocessed whole blood," Microfluid Nanofluid, vol. 10, pp. 697-702. (Year: 2011).*
Selvaraju et al., "Influenza and respiratory syncytial virus detection in clinical specimens . . . using FOCUS direct disc assay is substantially equivalent to the traditional methods and the FOCUS nucleic acid extraction-dependent RT-PCR assay," Diag. Micro. Infect. Dis., vol. 78, pp. 232-236. (Year: 2013).*
Tabb, Michelle, "Sinnplexa Direct Assays: Eliminating Extraction", FOCUS diagnostics slide presentation, retrieved on-line: http://nmgroup.ca/Document/2014/2014_01.pdf. (Year: 2019).*
3M Integrated Cycler brochure [retrieved on-line: https://www.focusdx.com/pdfs/brochures/DXIC0812_IC_Brochure.pdf; retrieval date: Apr. 19, 2019] (Year: 2019).*
International Search Report and Written Opinion dated Feb. 4, 2016, in PCT/US2016/062376.
Focke et al,. "Microstructuring of polymer films for sensitive genotyping by real-time PCR on a centrifugal microfluidic platform," Lab on a Chip, Oct. 7, 2010, 10:2519-2526.
Extended European Search Report dated Mar. 16, 2018 as issued in corresponding European Application No. 15863931.0.

* cited by examiner

*Primary Examiner* — Young J Kim
(74) *Attorney, Agent, or Firm* — Foley & Lardner LLP

(57) ABSTRACT

Disclosed are methods for identifying the presence or absence of a target nucleic acid from one or more organisms in a biological sample, said method comprising: (a) spinning the sample at a rotational velocity sufficient to pellet cellular debris and fluorescence inhibitors present within the sample and reduce fluorescence interference or quenching in the sample; and (b) directly amplifying and detecting the target nucleic acid in the sample.

18 Claims, 6 Drawing Sheets

AMPLIFICATION AND DETECTION OF NUCLEIC ACIDS IN A BIOLOGICAL SAMPLE

CROSS-REFERENCE TO RELATED APPLICATION

This application claims priority to and the benefit of U.S. Provisional Application No. 62/084,257, filed Nov. 25, 2014, the contents of which are incorporated herein by reference in their entirety.

FIELD OF THE INVENTION

The present invention relates to diagnostic and detection methods of nucleic acids for genetic testing and detection of organisms in a biological sample using direct amplification.

BACKGROUND OF THE INVENTION

The following discussion of the background of the invention is merely provided to aid the reader in understanding the invention and is not admitted to describe or constitute prior art to the present invention.

Nucleic acid detection in a biological sample such as whole blood often requires that the nucleic acid is extracted and purified from the sample prior to performing PCR. This is because constituents, such as hemoglobin in blood samples, and preserving reagents, such as anticoagulants, can interfere with PCR amplification (Wang, J-T., et al., 1992, J. Clin. Microbiol. 30:750). Target nucleic acids are particularly difficult to detect because the nucleic acids are typically present at much lower levels than endogenous nucleic acids such as genomic DNA or RNA transcribed therefrom. Extraction of nucleic acids of organisms from biological samples is time consuming and involves a high risk of contamination.

Given the high degree of complexity associated with isolating and detecting a nucleic acid molecule in a biological sample, it becomes increasingly desirable to detect the nucleic acid directly in a biological sample without any upstream nucleic acid extraction or extensive pre-processing step. Several methods have been reported for direct PCR of a pathogenic nucleic acid from blood samples, such as microwave irradiation (Ihhara, M., et al., 1994, BioTechniques 17(4):726), hydrogen peroxide treatment (Rudbeck, L. and Dissing, J., 1998, BioTechniques 25(4):588), and sodium hydroxide treatment (Queipo-Ortuna, M., et al., 1999, BioTechniques 27(2): 248). However, in cases where a quick diagnosis is sought, there is a need for quick methods that involve only a few steps and minimal technological requirements, and that still achieve consistent successful amplification of a nucleic acid in a biological sample.

SUMMARY OF THE INVENTION

The present invention is based on the discovery of methods that allow direct amplification of a nucleic acid in a whole blood sample without extracting the nucleic acid from the sample first. The methods of the invention involve the steps of subjecting a whole blood sample to rotation at high velocity to remove cellular debris and material that interfere with or quench fluorescence emission during PCR amplification, and directly amplifying and detecting the nucleic acid molecule.

Thus, the present invention provides methods for identifying the presence or absence of a target nucleic acid for genetic testing or detection of an organism in a biological sample, wherein the methods comprise (a) rotating a biological sample containing whole blood at a rotational velocity sufficient to pellet cellular debris and fluorescence inhibitors present within the sample and reduce fluorescence interference or quenching in the sample; and (b) directly amplifying and detecting the target nucleic acid in the sample. Preferably, the rotational velocity is in a range from greater than 140×g to 1500×g, and the biological sample is placed in a centrifugal microfluidic disc.

In one aspect of the invention, the detecting step comprises detecting a visible signal emitted through an optical path in the pelleted sample. Preferably, the detectable signal is a fluorescent emission. In another aspect of the invention, the step of amplifying comprises real-time polymerase chain reaction analysis. In a preferred embodiment, the target nucleic acid is DNA. In another preferred embodiment, the target nucleic acid is RNA.

In a preferred aspect of the invention, the biological sample is whole blood, and the target nucleic acid is from one or more organisms found in blood. In one aspect, the target nucleic acid is a human nucleic acid. In a different aspect, the target nucleic acid is from a microorganism. The microorganism can be a virus, such as an Ebola virus, a Marburg virus, an influenza virus, a respiratory syncytial virus, a varicella zoster virus, a herpes simplex virus, an enterovirus, a Dengue virus, or any combination thereof. In yet another aspect, the microorganism is a bacterium such as a gram-negative or a gram-positive bacterium. In a preferred embodiment, the bacterium is one or more of *Bacillus, Bordetella, Borrelia, Listeria, Escherichia, Salmonella, Campylobacter, Clostridium, Helicobacter, Mycobacterium, Staphylococcus, Camplobacter, Enterococcus, Neisseria, Shigella, Streptococcus, Vibrio, Yersinia*, and *Pseudomonas*, or any combination thereof. Preferably, the bacterium is *Bacillus anthracis*. In yet another embodiment, the microorganism is a fungus. Cellular debris may comprise lysed and intact red blood cells. The foregoing general description and the detailed description are exemplary and explanatory and are intended to provide further explanation of the invention as claimed. For detailed understanding of the invention, reference is made to the following detailed description of the preferred embodiments, taken in conjunction with the accompanying drawing. Other objects, advantages and novel features will be readily apparent to those skilled in the art from the following detailed description of the invention.

BRIEF DESCRIPTION OF THE FIGURES

FIG. 1 shows the disappearance of artifacts in the cycles between 5-30 in the spun samples.

Figure 1:
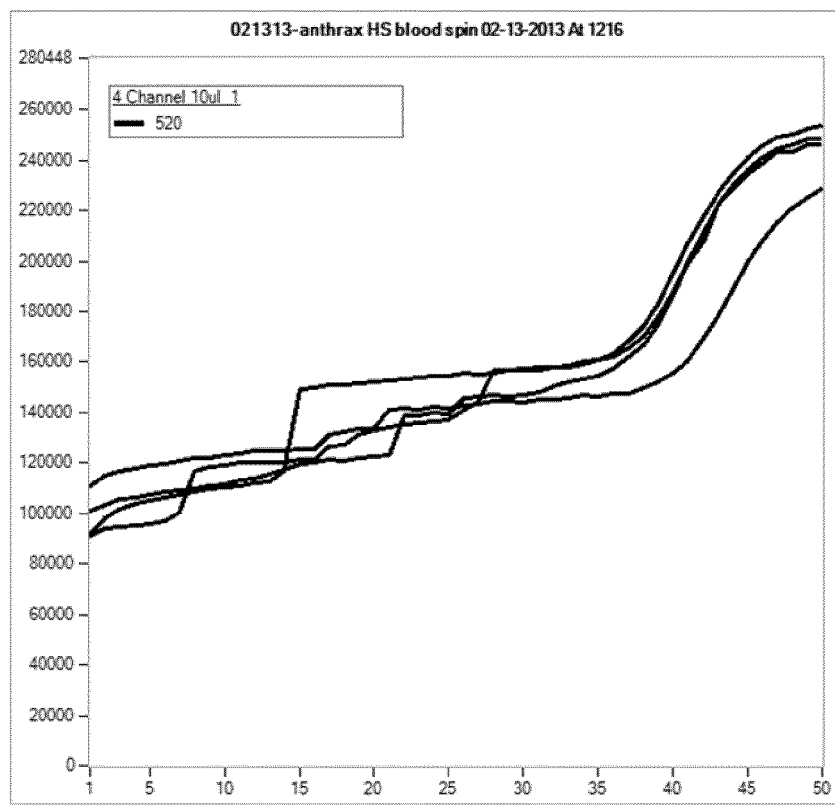
FIG. 1 shows the effect of high speed spinning on detection of artifacts. 50 copies per reaction of *Bacillus anthracis* chromosomal target were amplified from a whole blood sample (10% of the reaction volume) collected in an EDTA tube. Samples in the upper plot represents untreated samples while the lower plot represents samples that were spun off-board at about 900×g for 10 minutes at 23° C. as described in Example 1.
Figure 1:
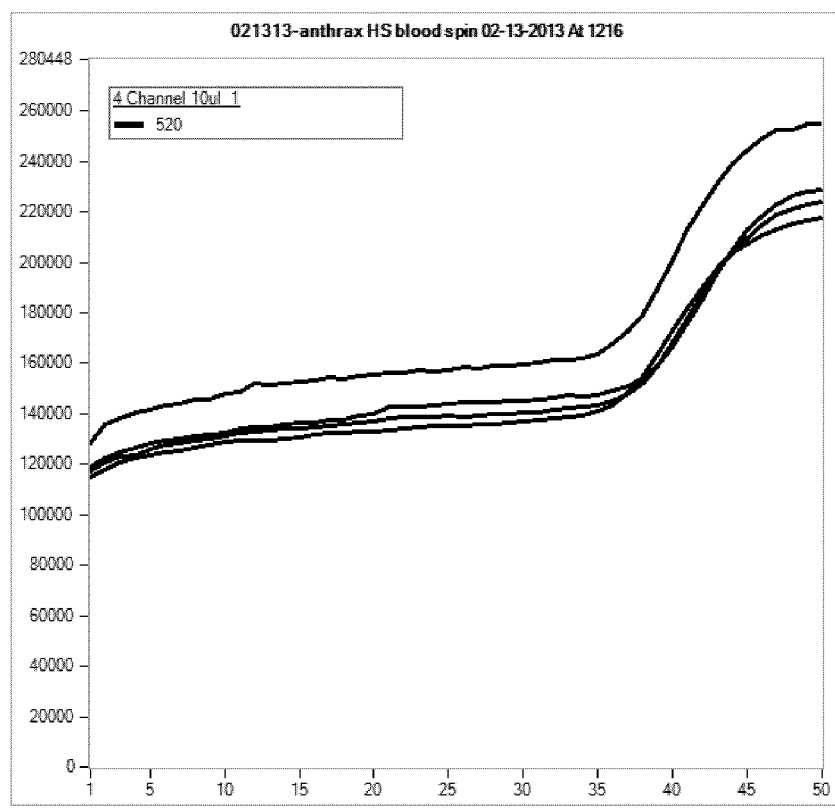
Figure 2:
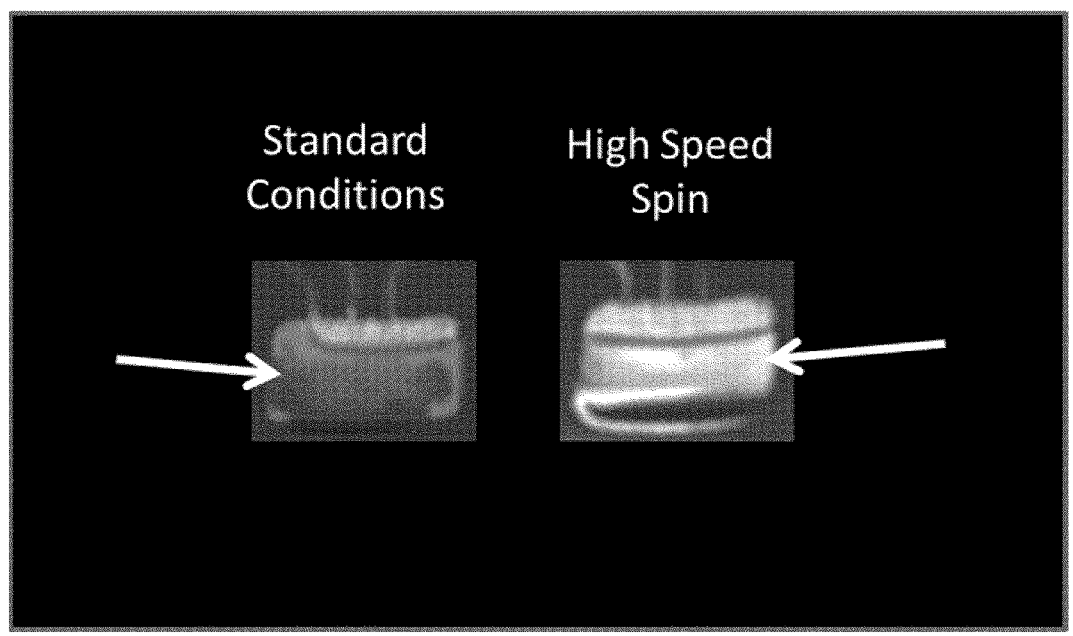
FIG. 2 are photographs of the centrifugal microfluidic discs referred to in Example 2. Exemplary individual wells (top) and the top view of the disc (bottom) are shown. The disc on the left was run using an assay definition that spun the samples at about 1500 rpm (about 140×g) during the whole assay, which is the standard methodology, and the disc on the right was run using a high speed definition which spun the samples at about 5000 rpm (1500×g) for the whole assay except during the optical reading step, when the samples were spun at the standard speed of about 1500 rpm (about 140×g). Blood particles can be observed throughout the well in the standard speed disc while the blood particles have pelleted to the periphery of the well in the high speed disc leaving the optical path in the middle of the well clear.
Figure 2:
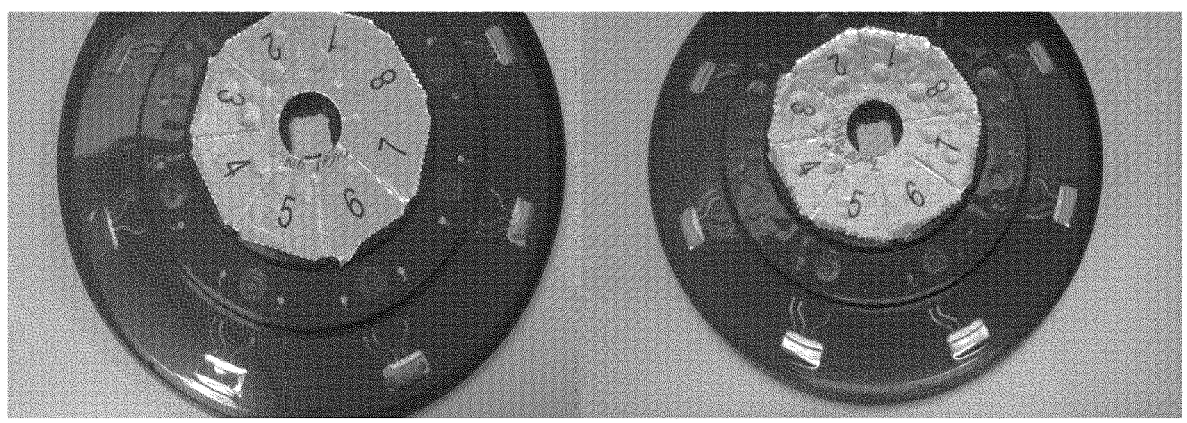

FIG. 4 shows RNA virus Ebola Reston amplification from whole blood using VHF high speed spin assay parameters.

FIG. 5 shows the effects of high speed spin on the area under the melt curve values in a genetic assay for a MTHFR 1298 heterozygote sample from whole blood. Two identical Universal Discs were prepared with reaction mixes including primers and Hybeacon™ probes for single nucleotide polymorphisms in the methylenetetrahydrofolate reductase (MTHFR) gene. The reaction consisted of 8 μL of reaction mix plus 2 μL of whole blood or buffer as the sample or 9 μL of reaction mix plus 1 μL of whole blood or buffer. Two discs were run using separate parameters: one with the standard PCR followed by melt analysis protocol (grey bars), and the other with the standard protocol but a high speed spin step added between the PCR cycles and the melt analysis step (black bars). The high speed spin increased the area under the melt curve values for the majority of the blood samples which results in an increased fluorescence intensity difference between the positive and negative samples.

FIG. 6 shows the melt curves for MTHFR 1298 heterozygote sample detection in whole blood. Standard Speed Spin (upper chart) and High Speed Spin (lower chart) parameters were used. High speed spin results in sharp peak differentiation for heterozygote determination as compared to standard speed.

DETAILED DESCRIPTION OF THE INVENTION

The present disclosure is directed to methods for identifying the presence or absence of a target nucleic acid in a biological sample without separating, extracting and purifying the nucleic acid first from the biological sample. The disclosed methods are based on the unexpected discovery that application of high centrifugal force to a whole blood sample causes pelleting of cellular debris and material that are present in the sample and that may otherwise interfere with the PCR reaction chemistry or with the emission of fluorescent light, such that real-time PCR amplification of the whole blood sample may be successfully achieved. The present inventors discovered that by adjusting the rotational velocity at which a rotating sample spins, cellular debris that may (i) inhibit the emission and/or detection of a detectable signal from the sample, (ii) interfere with or quench polymerase chain reaction chemistry itself, and/or (iii) obstruct the optical path through which a detectable signal travels during a real-time PCR assay, may be pelleted within the sample thus permitting effective amplification of the target nucleic acid and clearing an optical path through the sample, such that a visible amplification signal may be detected. As a result, the disclosed methods permit detection of a nucleic acid in a whole blood sample without extracting the nucleic acid from the sample.

In a preferred embodiment, the invention makes use of a 3M Integrated Cycler equipped with a consumable Direct Amplification Disc. The high rotational velocity achieved by the integration of the consumable disc into the 3M Integrated Cycler causes the cellular debris in the whole blood sample to move to and pellet at the periphery of the consumable disc, thus allowing the separation of cellular debris, including lysed and intact red blood cells and fluorescence inhibitors that normally cause quenching of the PCR reaction or interfere with fluorescence emission, and successful real-time PCR amplification of the whole blood sample. Preferably, the relative centrifugal force is from about 0×g to about 1500×g.

In alternative embodiments, a high centrifugal force is applied to a multiplexed compact disc platform on which the whole blood sample is placed for testing, and the cellular debris are separated by spinning at high angular velocities, such as 1500×g.

Definitions

As used herein, the term "DNA" refers to a nucleic acid molecule comprising a deoxyribose sugar as opposed to a ribose sugar as found in RNA.

As used herein, the term "RNA" refers to a nucleic acid molecule comprising a ribose sugar as opposed to a deoxyribose sugar as found in DNA. As used herein, RNA refers to all species or RNA including messenger RNA (mRNA), ribosomal RNA (rRNA), transfer RNA (tRNA), as well as small RNA species that have regulatory function. "Small RNA species" have a specific meaning and refer to untranslated RNAs with housekeeping or regulatory roles in bacteria. "Small RNA species" are not rRNA or tRNA.

As used herein, the term "target nucleic acid" refers to any nucleic acid molecule or fragment that is a target for detection in a sample. In some embodiments, a target nucleic acid is of viral, bacterial, or fungal origin. In different embodiments, the target nucleic acid molecule is of human origin. Target nucleic acids may be DNA or RNA molecules.

As used herein, the term "cycling" or "thermocycling" refers to any technique by which a laboratory apparatus is used to amplify segments of a nucleic acid sequence with a primer extension reaction using pre-programmed cycles of raised and lowered temperatures. Examples of thermocycling include, but are not limited to PCR, real-time PCR, and reverse transcription-polymerase chain reaction (RT-PCR).

As used herein, the term "reverse transcriptase-polymerase chain reaction" or "RT-PCR" refers to any technique for synthesizing and amplifying a DNA molecule with a sequence that is a copy of an RNA sequence. RT-PCR is useful in detecting RNA species such as in quantitative analysis of gene expression, as well as for producing DNA copies of RNA for use in cloning, cDNA library construction, probe synthesis, and signal amplification in in situ hybridizations.

As used herein, the term "reagent mix" or "reaction mixture" or "reaction mix" refers to a composition having all the elements required to perform reverse transcription and/or reverse transcription polymerase chain reaction, or real-time polymerase chain reaction, including but not limited to primers having specificity for the sequence of the diagnostic target RNA or DNA, respectively, and a polymerase.

As used herein, the term "amplification mixture" is a mixture of reagents that are used in a nucleic acid amplification reaction, but does not contain primers or sample. An amplification mixture comprises a buffer, dNTPs, and a DNA polymerase. An amplification mixture may further comprise at least one of $MgCl_2$, KCl, nonionic and ionic detergents.

As used herein, the term "amplification master mix" comprises an amplification mixture and primers for amplifying a target nucleic acid, but does not contain a sample to be amplified.

As used herein, the term "reagent-sample mixture" refers to a mixture containing reagent mix plus sample.

As used herein, "primer" refers to an oligonucleotide, synthetic or naturally occurring, which is capable of acting as a point of initiation of nucleic acid synthesis or replication along a template strand when placed under conditions in which the synthesis of a complementary strand is catalyzed by a polymerase. Within the context of reverse transcription, primers are composed of nucleic acids and prime on RNA templates. Within the context of PCR, primers are composed of nucleic acids and prime on DNA templates.

As used herein, the term "DNA polymerase" refers to any enzyme that helps catalyze in the polymerization of deoxyribonucleotides into a DNA strand. DNA polymerases act to add free nucleotides to the 3' end of a newly-forming strand, resulting in elongation of the new strand in a 5'-3' direction.

As used herein "TaqMan®" refers to a method for real-time PCR. In this method, a TaqMan® probe which hybridizes to the nucleic acid segment amplified is included in the PCR reaction mix. The TaqMan® probe comprises a donor and a quencher fluorophore on either end of the probe and in close enough proximity to each other so that the fluorescence of the donor is taken up by the quencher. However, when the probe hybridizes to the amplified segment, the 5'-3' exonuclease activity of the Taq polymerase cleaves the probe thereby allowing the donor fluorophore to emit fluorescence which can be detected.

As used herein, "lysis" means perturbation or alteration to a cell wall or viral particle facilitating access to or release of the cellular RNA or DNA. Neither complete disruption nor breakage of the cell wall is an essential requirement for lysis.

As used herein, the term "cycle threshold" or "Ct" refers to the cycle during thermocycling in which the increase in fluorescence due to product formation reaches a significant and detectable level above background signal.

As used herein, the term "direct amplification" refers to a nucleic acid amplification reaction in which the target nucleic acid is amplified from the sample without prior purification, extraction, or concentration. It is a relative measure of the concentration of target in the PCR reaction. Many factors impact the absolute value of Ct besides the concentration of the target. However, artifacts from the reaction mix or instrument that change the fluorescence measurements associated with the Ct calculation will result in template-independent changes to the Ct value.

As used herein, the term "extraction" refers to any action taken to remove a nucleic acid from other (non-nucleic acid) material present in the sample. Such action includes, but is not limited to, mechanical or chemical lysis, addition of detergent or protease, or precipitation and removal of a non-nucleic acid such as a protein.

As used herein, the term "interfering substance" refers to any substance in a sample that is not a target nucleic acid. Such interfering substances include synthetic and biological substances. Such synthetic substances include chemicals and pharmaceutical drugs. Such biological substances include blood, urine, proteins and other biological molecules.

As used herein, the term "fluorescence inhibitors" refers to cellular components, cellular debris and materials that may substantially interfere with or quench fluorescence emission.

As used herein, the term "rotational velocity" or "rotational speed" or "spin speed" or "spinning speed" refers to the number of complete rotations, revolutions, cycles, or turns around a center point per time unit. Preferably, the relative centrifugal force is from about 140×g to about 1500×.

As used herein, the terms "amplification" or "amplify" includes methods for copying a target nucleic acid, thereby increasing the number of copies of a selected nucleic acid sequence. Amplification may be exponential or linear. A target nucleic acid may be either DNA or RNA. The sequences amplified in this manner form an "amplicon." While the exemplary methods described hereinafter relate to amplification using the polymerase chain reaction (PCR), numerous other methods are known in the art for amplification of a nucleic acid (e.g., isothermal methods, rolling circle methods, etc.). The skilled artisan will understand that these other methods may be used either in place of, or together with, PCR methods. See, e.g., Saiki, "Amplification of Genomic DNA" in PCR Protocols, Innis et al., Eds., Academic Press, San Diego, Calif. 1990, 13-20; Wharam, et al., Nucleic Acids Res. 2001, 29(11):E54-E54; Hafner, et al., Biotechniques 2001, (4):852-6, 858, 860 passim; Zhong, et al., Biotechniques 2001, 30(4):852-6, 858, 860.

As used herein, the term "detecting" used in context of detecting a signal from a detectable label to indicate the presence of a target nucleic acid in the sample does not require the method to provide 100% sensitivity and/or 100% specificity. As is well known, "sensitivity" is the probability that a test is positive, given that the person has a target nucleic acid, while "specificity" is the probability that a test is negative, given that the person does not have the target nucleic acid. A sensitivity of at least 50% is preferred, although sensitivities of at least 60%, at least 70%, at least 80%, at least 90% and at least 99% are clearly more preferred. A specificity of at least 50% is preferred, although sensitivities of at least 60%, at least 70%, at least 80%, at least 90% and at least 99% are clearly more preferred. Detecting also encompasses assays with false positives and false negatives. False negative rates may be 1%, 5%, 10%, 15%, 20% or even higher. False positive rates may be 1%, 5%, 10%, 15%, 20% or even higher.

As used herein, the term "sample" or "test sample" may comprise clinical samples, an isolated nucleic acid, or an isolated microorganism. In preferred embodiments, a sample is obtained from a biological source (i.e., a "biological sample"), such as tissue, bodily fluid, or microorganisms collected from a subject. Sample sources include, but are not limited to, sputum (processed or unprocessed), bronchial alveolar lavage (BAL), bronchial wash (BW), blood, whole blood, bodily fluids, cerebrospinal fluid (CSF), urine, plasma, serum, or tissue (e.g., biopsy material). Preferred sample sources include nasopharyngeal swabs, wound swabs, and nasal washes. The term "patient sample" as used herein refers to a sample obtained from a human seeking diagnosis and/or treatment of a disease.

As used herein, the term "primer-probe detection system" refers to a method for real-time PCR. This method utilizes a bi-functional molecule (referred to herein as a primer-probe), which contains a PCR primer element covalently linked by a polymerase-blocking group to a probe element. Additionally, each primer-probe molecule contains a fluorophore that interacts with a quencher to reduce the background fluorescence. Primer-probes, as used herein, may comprise a 3' primer with a 5' extended probe tail comprising a hairpin structure which possesses a fluorophore/quencher pair. During PCR, the polymerase is blocked from extending into the probe tail by the inclusion of hexaethylene glycol (HEG). During the first round of amplification the 3' target-specific primer anneals to the target nucleic acid and is extended such that the primer-probe is now incorporated into the newly synthesized strand, which possesses a newly synthesized target region for the 5' probe. During the next round of denaturation and annealing, the probe region of the primer-probe hairpin loop will hybridize to the target, thus separating the fluorophore and quencher and creating a measurable signal. Such primer-probes are described in Whitcombe et al., Nature Biotech 17: 804-807 (1999). Scorpion® probes are exemplary primer-probes.

Biological Samples

Biological samples in which a target nucleic acid can be detected using the disclosed methods may be from sterile and/or non-sterile sites and include body fluids such as whole blood, plasma, serum, cell free plasma, urine, cerebrospinal fluid (CSF), synovial fluid, pleural fluid, pericardial fluid, intraocular fluid, and stool sample that potentially contain a nucleic acid. In one embodiment, the biological sample is whole blood. As used herein, "cell-free plasma" indicates plasma containing less than 1% cells by volume.

A biological sample may be suspected of containing a target nucleic acid. A target nucleic acid may be RNA and/or DNA. In some embodiments a target nucleic acid is from a microorganism such as a bacterium, a fungus or a virus. In other embodiments the target nucleic acid is from a human. In addition, a biological sample may be obtained from an individual suspected of being infected with a microorganism such as a bacterium, fungus or virus. In some embodiments a target nucleic acid may be an endogenous nucleic acid such as a gene or a transcript (RNA). In some embodiments the target nucleic acid is a mutant form of a gene or transcript or a particular single nucleotide polymorphism (SNP).

The disclosed methods preferably employ unprocessed biological samples (i.e., a biological sample containing endogenous nucleic acids; and/or a biological sample from which nucleic acids have not been extracted), thus resulting in a direct, streamlined sample-to-answer process. However, the detection methods disclosed herein also are effective if used on isolated nucleic acid (DNA and/or RNA) purified from a biological sample according to any methods well known to those of skill in the art.

Target Nucleic Acids

A target nucleic acid may be DNA (including genomic DNA) or RNA. Further, a target nucleic acid may be any nucleic acid found in a microorganism or a human host. DNA includes, for example, DNA derived from humans, bacterial species, fungus, and DNA viruses. Viral DNA suitable for assessment includes DNA obtained directly from the viral capsid as well as DNA integrated into the host genome.

RNA types that may be assayed as a target nucleic acid include rRNA, mRNA, transfer-RNA (tRNA), or other RNA polynucleotides. Species of rRNA include 5S, 16S, and 23S polynucleotides, which may contain one or more sub-sequences characteristic of a group of related bacteria. The detection capacity of the characteristic sequence is variable and depends on the level of relatedness of the virus or bacteria to be detected by the assay. Other RNA polynucleotides may be used as target RNA. Primers may be designed by one skilled in the art to prime the synthesis of a copy DNA using the target RNA as template in a reverse transcription reaction.

One skilled in the art will also know how to design a pair of primers for the amplification of the target DNA or target RNA using the copy DNA as template in PCR. It is well known in the art that primers used synchronously in PCR should have similar hybridization melting temperatures.

Reverse Transcription and Real-Time PCR

Amplification of Nucleic Acids

A target nucleic acid in a biological sample may be amplified by various methods known to the skilled artisan. Preferably, PCR is used to amplify a target nucleic acid of interest. In this method, two or more oligonucleotide primers that flank or include, and anneal to opposite strands of a nucleic acid of interest are repetitively annealed to their complementary sequences, extended by a DNA polymerase (e.g., AmpliTaq Gold polymerase), and heat denatured, resulting in exponential amplification of the target nucleic acid sequence. Cycling parameters can be varied, depending on the length of the nucleic acid to be extended. The skilled artisan is capable of designing and preparing primers that are appropriate for amplifying a target sequence in view of this disclosure. The length of the amplification primers for use in the present invention depends on several factors including the nucleotide sequence identity and the temperature at which the nucleic acid is hybridized or used during in vitro nucleic acid amplification. The considerations necessary to determine a preferred length for an amplification primer of a particular sequence identity are well known to the person of ordinary skill. For example, the length of a short nucleic acid or oligonucleotide can relate to its hybridization specificity or selectivity.

Methods that do not require a separation step prior to detection of an amplified nucleic acid product are commonly referred to as Real-Time PCR or homogeneous detection. Most real-time methods detect amplified product formation by monitoring changes in fluorescence during thermocycling. These methods include but are not limited to: TAQMAN® dual labeled probes (Applied Biosystems, Foster City, Calif. 94404), Molecular Beacons (Tyagi S and Kramer FR (1996) Nat Biotechnol 14:303-308), and SYBR® Green dye (Molecular Probes, Inc. Eugene, Oreg. 97402-0469). Some of these same methods can be used for end point detection of amplified products as well. An example of this type of method is SYBR® Green dye dissociation curve analysis. In dissociation curve analysis a final slow ramp in temperature, combined with fluorescence monitoring can detect the melting point and thereby the presence of an amplified product (Ririe et al., 1997, Anal. Biochem. 245: 154-60).

In the present methods, the presence of a target nucleic acid may be tested by reverse transcription (RT) and polymerase chain reaction (PCR). When used together, reverse transcription and polymerase chain reaction may be performed sequentially in two steps, or together in one step with all reaction composition reagents being added to the sample.

In a two-step method, incubation of a sample in a reverse transcription reaction composition allows a DNA copy from the target RNA to be synthesized. The reagent mix includes a primer that hybridizes to the target RNA to prime the synthesis of the copy DNA. In addition, the reagent mix includes dNTPs, $MgCl_2$, KCl, a reverse transcriptase and a reverse transcriptase buffer. More than one primer may be included if it is desired to make DNA copies from more than one target RNA. The product of the reverse transcription reaction may then be transferred to another assay tube where PCR is performed according to protocol well known in the art. The PCR composition typically includes a pair of primers that initiate synthesis of the desired segment of DNA from the reverse transcribed template. In addition, the PCR mix usually comprises of dNTPs, $MgCl_2$, KCl, a thermostable DNA polymerase such as Taq polymerase, and polymerase buffer. More than one pair of primers may be included if synthesis of multiple segments of DNA is desired. Also a single new primer may be added that will amplify a DNA segment with the original RT primer as the second primer of the pair. Additional reverse transcriptases that may be used for viral samples include, but are not limited to, HIV Reverse Transcriptase (Ambion), Transcriptor Reverse Transcriptase (Roche), Thermoscript Reverse Transcriptase (Invitrogen). Additional DNA polymerases that may be used include, but are not limited to, Pfu, Vent, and Sequitherm DNA Polymerase (EPICENTRE).

In one embodiment of the present invention, a biological sample is combined with an RT-amplification mixture so that RT and PCR can be carried out in a single assay.

Regardless of whether the RT-PCR is carried out as two steps or one step, the RT step is run first and typically consists of a single temperature incubation at a temperature of between about 37° C. and about 70° C. Different temperatures are appropriate for different RT enzymes and different primers, as is known to one skilled in the art. The subsequent PCR reaction typically consists of an initial incubation at about 94° C. to about 97° C. for about 2 to about 15 minutes. This step is used to denature the cDNA and also to activate heat activated Taq polymerase enzymes. This is then followed by multiple cycles of amplification of the cDNA target. Three operations are performed during each cycle: target denaturation, primer annealing and primer extension. Target denaturation typically occurs at greater than about 90° C. Primer annealing temperature is dictated by the melting temperature of the specific primers used in the reaction and primer extension is performed at temperatures ranging from about 50° C. to about 72° C. depending on the thermostable polymerase being used. When primer annealing and extension are performed at the same temperature, this is a two temperature PCR compared with a three temperature PCR in which each of the three steps occur at a different temperature. After the amplification phase is complete, a final extension time is typically added to ensure the synthesis of all amplification products.

The biological sample is loaded directly into a centrifugal microfluidic disc well or compartment or into a gene rotor disc compartment without a separate, front-end specimen preparation, followed by reverse transcription and real-time-PCR amplification and detection of a target nucleic acid (if present in the sample) in the same disc. An internal positive amplification control (IPC) can be included in the sample, utilizing oligonucleotide primers and probes.

In some embodiments, the PCR is a multiplex PCR reaction. The integrated thermal cycler may heat at >5° C. per second, cool at >4° C. per second, and allow for the cycling parameters to be varied, depending on the length of the amplification products to be extended.

Rotary Platform Technology

The disclosed methods may be performed using any thermal cycler with a rotating platform that is capable of centrifuging or rotating a sample along a curved path around a central point at a high rotational velocity. The rotational velocity must be sufficient to move the cellular debris in the biological sample or the reagent-sample mixture to a section within the sample compartment—preferably forming a pellet—thus sequestering debris that inhibit the emission and/or detection of a detectable signal from the sample, interferes with or quenches polymerase chain reaction chemistry itself, and/or obstructs the optical path through which a detectable signal travels during a real-time PCR assay. By "high rotational velocity" it is meant a rotational speed greater than 140 g. Preferably, the relative centrifugal force is from about 140×g to about 1500×g.

In some embodiments a sample is contained in a compartment of a centrifugal microfluidic disc during amplification cycles. As used herein, a "centrifugal microfluidic disc" is a circular disc that spins on its axis within a thermal cycler and contains compartments in which a biological sample can be deposited. Exemplary centrifugal microfluidic discs are the Direct Amplification Discs (8 wells) and the Universal Disc (96 wells) from Focus Diagnostics that are utilized in conjunction with a 3M™ Integrated Cycler themal cycler sold by 3M (St. Paul, Minn., USA). The 3M™ Integrated Cycler can receive a Direct Amplification Disc and is capable of performing multiple assays per disc. In some embodiments a biological sample is deposited in a gene rotor disc. Preferably, the biological sample is a whole blood sample. As used herein, a "gene rotor disc" is a centrifuge rotor insert that holds tubes or other compartments that can house samples and/or sample-amplification mixtures at a uniform temperature. Examples of a gene rotor disc are the Qiagen Rotor Discs and/or Gene Discs that are utilized with the Qiagen Rotor-Gene Q thermal cycler.

In some embodiments a whole blood sample is deposited in a disc compartment (or well) separate from a disc compartment in which a reagent mixture is deposited. In this embodiment the sample and reagent mixture may subsequently be combined in the disc to permit amplification of the target nucleic acid if present. In some embodiments, the reagent mixture and sample are combined prior to depositing in a centrifugal microfluidic disc or gene rotor disc. In some embodiments, real-time PCR amplification and detection is performed using the Simplexa Direct assay in a Direct Amplification Disc and is performed in thermal cycler such as the 3M™ Integrated Cycler. Alternatively, PCR amplification and detection may be performed using the Pall GENEDISC® or the GenePOC diagnostic system.

Rotational velocity achieved using a centrifugal microfluidic disc and associated thermal cycler, a gene rotor disc and associated thermal cycler, or any other thermal cycler with a rotating platform capable of creating such a rotational velocity can be used to pellet the cellular debris from the biological sample. The cellular debris is sequestered, preferably pelleted, to the periphery of a sample compartment. The cellular debris from the biological sample includes, but is not limited to, lysed and intact red blood cells, florescence inhibitors, and reagents that may otherwise interfere with or quench the PCR reaction chemistry itself or interfere with the optical path necessary to read fluorescence emitted during real-time PCR assays.

Increasing the rotational velocity or the spin speed of centrifugal microfluidic disc or gene rotor disc is required for direct detection and amplification of a target nucleic acid in a whole blood sample. The present inventors discovered that using the 3M™ Integrated Cycler under normal operating conditions with spin speeds set by the manufacturer did not allow successful real-time PCR amplification from whole blood patient samples.

The present disclosure is directed to modification of system parameters, which allow pelleting of the debris for successful amplifications of a nucleic acid without extraction of the nucleic acid from the whole blood sample. The present disclosure is also directed to spin speeds during certain steps of the real-time PCR assay that were optimized and modified to allow clearance of the optical path before real-time PCR fluorescence emissions were determined at each cycle. The Tables below show the rotational speed for each of the steps in real-time PCR steps. Rotational speed can be introduced at any stages of the PCR cycling parameters (Table 1). Fast spinning can be performed during the whole run except before reading fluorescence at each cycle (Table 1), or at any stages of the PCR cycling before reading fluorescence during the anneal/extend step (Table 2-4).

TABLE 1

Valving and Spinning Parameters

| Step | Temperature (° C.) | Time (Seconds) | Cycles | Speed (g)** |
|---|---|---|---|---|
| Mixing* | 45 | 120 | 1 | 30-1100 |
| Initial Denaturation | 97 | 120 | 1 | 1500 |
| Denaturation | 97 | 15 | 50 | 1500 |
| Anneal/Extend | 60 | 15 | | 1500 |
| Anneal/Extend/Detection | 60 | 15 | | 140 |

*Option to valve reaction mix or sample first prior to mixing. Preferential valving can improve consistent results, especially near Limit of Detection.
**Spin speed settings can be introduced at various stages of PCR cycling parameters.

TABLE 2

Finalized Assay Definitions for Bacillus anthracis

| Step | Temperature (° C.) | Time (Seconds) | Cycles | Speed (g) |
|---|---|---|---|---|
| Mixing | 45 | 120 | 1 | 30 to 1100 |
| Initial Hold | 45 | 120 | 1 | 1500 |
| Initial Denaturation | 97 | 120 | 1 | 1500 |
| Denaturation | 97 | 10 | 45 | 140 |
| Anneal/Extend/Detection | 60 | 20 | | |

TABLE 3

Finalized Assay Definitions for Viral Hemorrhagic Fever

| Step | Temperature (° C.) | Time (Seconds) | Cycles | Speed (g) |
|---|---|---|---|---|
| Reverse Transcription | 50 | 780 | 1 | 140 |
| | 50 | 120 | | 1500 |
| Initial Denaturation | 97 | 120 | 1 | 1500 |
| Denaturation | 97 | 15 | 45 | 140 |
| Anneal/Extend | 58 | 22 | | |
| Anneal/Extend/Detection | 58 | 8 | | |

TABLE 4

Finalized Assay Definitions for Coagulation Melt Assay

| Step | Temperature (° C.) | Time (Seconds) | Cycles | Speed (g) |
|---|---|---|---|---|
| Initial Denaturation | 97 | 120 | 1 | 1500 |
| Denaturation | 97 | 10 | 50 | 140 |
| Anneal/Detection | 49 | 20 | | 140 |
| Extend | 60 | 40 | | 140 |
| Hold | 30 | 600 | 1 | 1500 |
| Melt Analysis | 30-70 | 10 | 1 | 140 |

The present disclosure is the first report of a real-time PCR system with the ability to use high rotational velocity to remove cellular debris and inhibitors for direct PCR reactions. The disclosed methods demonstrate improved detection and consistency of melting curve analysis performed using human DNA directly amplified from whole blood as illustrated in Example 3.

The high speed spin assay is performed by increasing the relative centrifugal force from about 140×g to about 1500×g of, for example, a centrifugal microfluidic disc such as the Direct Amplification Disc. The rotational velocity necessary to sufficiently pellet/sequester cell debris may be different for a centrifugal microfluidic disc or a gene rotor disc having a different radius. Once the process is found to be beneficial, further optimization of the spin speed parameters on a per assay basis may be done. The methods disclosed in the present invention can amplify a nucleic acid directly from any biological sample without an additional step of extraction and purification of the nucleic acid. The software controls the speed of rotation, such that nucleic acids from different organisms may be separated and detected in the whole blood sample. The duration of rotation varies with the speed of rotation. Higher speed requires shorter rotation cycles. Thus, rotation at 1500×g leads to complete separation of debris from the sample in two minutes. Further optimization of the spin speed parameters on a per assay basis may be performed. This method has been successfully applied by the present inventors to amplify a nucleic acid directly from whole blood in an assay to detect *Bacillus anthracis*, a Viral Hemorrhagic Fever panel, a Dengue fever serotyping assay, and to detect a single nucleotide polymorphism (SNP).

In some embodiments, the 3M™ Integrated Cycler or an equivalent is used together with Direct Amplification Disc consumable or an equivalent and direct chemistry to create increased rotational velocity allowing direct detection of DNA and RNA from a biological sample, such as a whole blood specimen. Examples of successful detections include, but are not limited to, DNA targets in the bacterial pathogen *Bacillus anthracis*, and the RNA viruses Ebola and Marburg.

Detectable Signals

In the disclosed methods, the presence or absence of a target nucleic acid in a whole blood sample is determined by detecting a signal generated by amplification of the target nucleic acid, if present in the sample. Detectable signal emission during nucleic acid amplification is a hallmark of real-time polymerase chain reaction. Thus, in one embodiment, a sample is subjected to a real-time PCR reaction and the presence of a target nucleic acid is detected by detecting a detectable label if the target nucleic acid is present in the sample.

One general method for real-time PCR uses a fluorescent probe, such as the TaqMan® probe, a molecular beacon and scorpions. In some embodiments the real-time PCR reaction involves the use of a quencher/donor probe detection system such as the TaqMan® PCR detection system. As used herein a "quencher/donor probe detection system" refers to a method for real-time PCR wherein the reagent master mix includes a quencher/donor probe which hybridizes to the target nucleic acid to be amplified. The quencher/donor probe (such as a TaqMan® probe) comprises a donor and a quencher fluorophore on either end of the probe and in close enough proximity to each other so that the fluorescence of the donor is taken up by the quencher. However, when the probe hybridizes to the amplified segment, the 5'-3' exonuclease activity of the Taq polymerase cleaves the probe thereby allowing the donor fluorophore to emit fluorescence which can be detected.

Real-time PCR quantitates the initial amount of the template with more specificity, sensitivity and reproducibility, than other forms of quantitative reverse transcriptase PCR, which detect the amount of final amplified product. Real-time RT-PCR does not detect the size of the amplicon. The probes employed in TaqMan® and molecular beacon technologies are based on the principle of fluorescence quenching and involve a donor fluorophore and a quenching moiety.

In some embodiments, the detectable label is a fluorophore. The term "fluorophore" as used herein refers to a molecule that absorbs light at a particular wavelength (excitation frequency) and subsequently emits light of a longer wavelength (emission frequency). The term "donor fluorophore" as used herein means a fluorophore that, when in close proximity to a quencher moiety, donates or transfers emission energy to the quencher. As a result of donating energy to the quencher moiety, the donor fluorophore will itself emit less light at a particular emission frequency that it would have in the absence of a closely positioned quencher moiety.

Primer-probes, such as Scorpions, or Taqman and Hybeacon probes may be used to perform the methods according to the invention. Other real-time PCR fluorescent amplification technologies may also be applied by one who is skilled in the art.

The probe may be detectably labeled using methods known in the art. Other useful labels include, e.g., fluorescent dyes (e.g., Cy5®, Cy3®, FITC, rhodamine, lanthamide phosphors, Texas red, a carboxyfluorescein fluorophore such as fluorescein amidite (FAM), JOE, a xanthene dye such as Cal Fluor Red 610® ("CFR610") and Quasar 670® that fluoresces in the red region of the visible spectrum and can be effectively quenched by a quencher such as a Black Hole Quencher™ (BHQ™), BHQ-1, BHQ-2 and BHQ-3. The label can be attached to the oligonucleotide probe that hybridizes or binds to the target nucleic acid to be detected.

In some embodiments the detectable signal from the sample is read while the sample is rotating in the thermal cycler. The detectable signal is read through a cleared optical path in the sample after the cell debris has been pelleted or sequestered, thus reducing background fluorescence and reducing undesirable amplification curve variations, which can cause false reading and/or mask amplification curves. See US Patent Application Publication Nos. 2011/0117656 and 2012/0171677, the contents of which are herein incorporated in their entirety. In some embodiments the detectable signal from the pelleted sample is read shortly after rotation of the sample decreases. Preferably, high speed spinning is done only prior to thermocycling, and the sample is rotated at low speed (about 140×g) during optimal reading to allow optical reading before high speed spinning is resumed. In alternative embodiments, the samples are rotated at high speed (15008×g) during the entire assay.

Assay Sensitivity

The sensitivity of some amplification assays using unprocessed samples can be increased by adding one or more sensitivity-increasing components to the buffer used in the assays. Such components include, but are not limited to, KCl, a surfactant and albumin. In some embodiments, the albumin is bovine serum albumin. In some embodiments, the surfactant is a cationic surfactant. The sensitivity of the direct amplification assays also can be increased by providing additional heating, such as pre-heating a sample before adding the reagents. In some embodiments, the sensitivity can be increased by a combination of the sensitivity-increasing components and additional heating.

EXAMPLES

The present methods, thus generally described, will be understood more readily by reference to the following examples, which are provided by way of illustration and are not intended to be limiting of the present methods and kits.

Example 1

Off-Board Spinning Experiments of Whole Blood

Experiments involving off-board centrifugation of whole blood samples were performed. The samples were spun at 900×g for 10 minutes at 23° C. The results show that the centrifugation of the blood samples with a pre-spin reduces the variation in background fluorescence and undesirable amplification curve, whereas blood samples without a pre-spin do not have a reduced variation in the background of fluorescence (FIG. 1).

Example 2

Effect of Centrifugal Microfluidic Disc High Speed Spin on Detection of Viral RNA or Bacterial DNA in Whole Blood Increasing the rotational velocity or the spin speed of the centrifugal microfluidic disc on the 3M Integrated Cycler system produced unexpected results. A specially designed software was used to control the rotational velocity or spin speed in a range from about 140×g to about 1500×g. Further optimization of the spin speed parameters on a per assay basis was done as illustrated below. This method has been successfully applied to amplify a nucleic acid directly from whole blood in an assay to detect *Bacillus anthracis*, a Viral Hemorrhagic Fever panel, and a Dengue fever serotyping assay as shown below.

A. Dengue Virus Spiked Blood

Inactivated Dengue virus was diluted in whole blood or PBS buffer. The identical samples were run with an assay definition that spun the samples at about 1500 rpm (about 140×g) during the whole assay, which is the standard methodology, and another assay definition which spun the samples at about 5000 rpm (1500×g) for the whole assay except during the optical reading step, when the samples were spun at the standard speed of about 1500 rpm (about 140×g).

TABLE 5

Effects of rotational speed on the Ct Values of the Dengue Virus Target

| | Speed | |
| --- | --- | --- |
| | 1500 rpm | 5000 rpm |
| | (140 × g) | (1500 × g) |
| Samples | Ct Values | |
| Buffer 1 | 31.0 | 29.5 |
| Buffer 2 | 31.0 | 29.8 |
| Blood 1 | Not Detected | 34.4 |
| Blood 2 | Not Detected | 33.9 |
| Blood 3 | 38.3 | 33.0 |
| Blood 4 | 37.4 | 34.3 |
| Blood 5 | 35.8 | 35.2 |
| Blood 6 | 36.0 | 34.0 |

B. *Bacillus anthracis*

Figure 3:
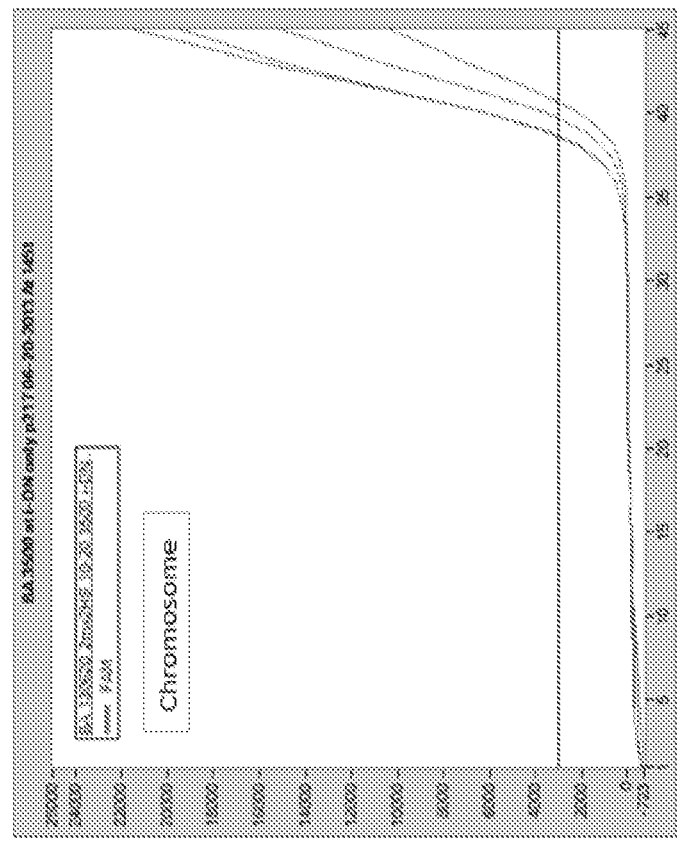
FIG. 3 shows the results for detection of a bacterial chromosome target from *Bacillus anthracis* in whole blood during optimization of high speed spin assay parameters. Samples were run using two different high speeds and durations. Samples were spun at 2500 rpm (780×g) for six minutes (A) versus 3500 rpm (1500×g) for two minutes (B) at the beginning of the run followed by spinning at the standard speed of about 1500 rpm (about 140×g) for the remainder of the run. Amplification curves and average Ct values from varying the initial spin speed and duration are shown.
Figure 3:
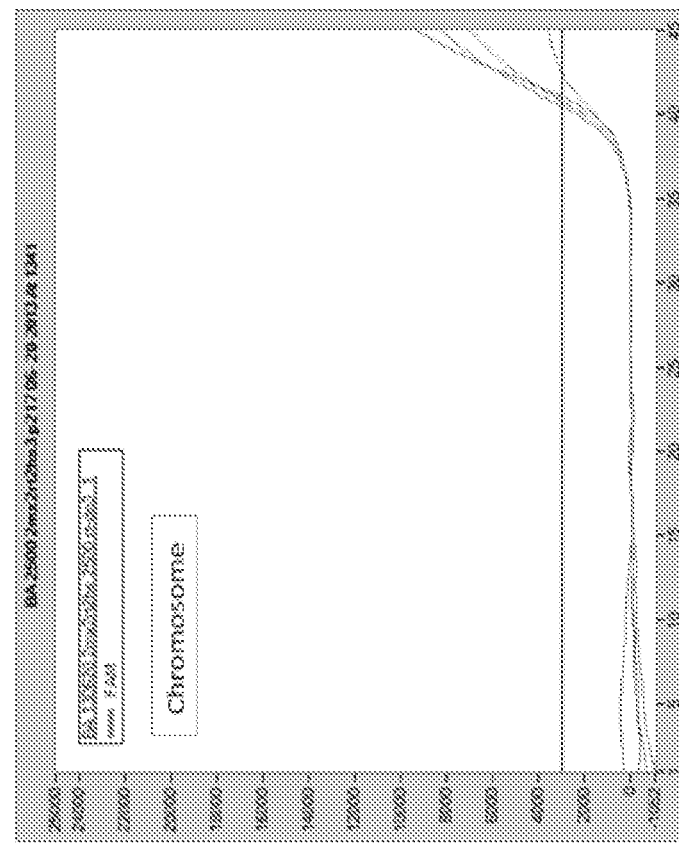
Figure 4:
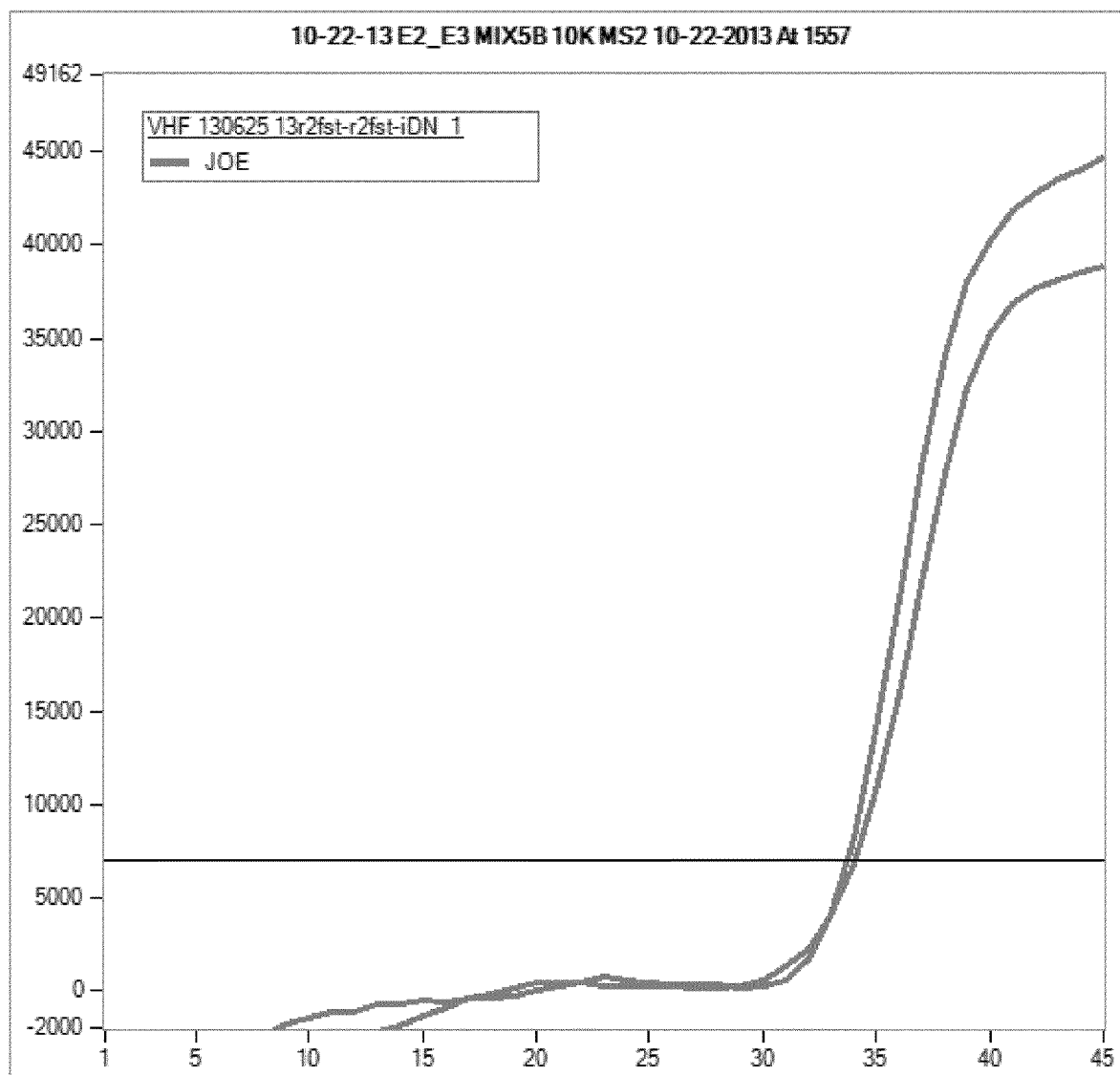
Figure 5:
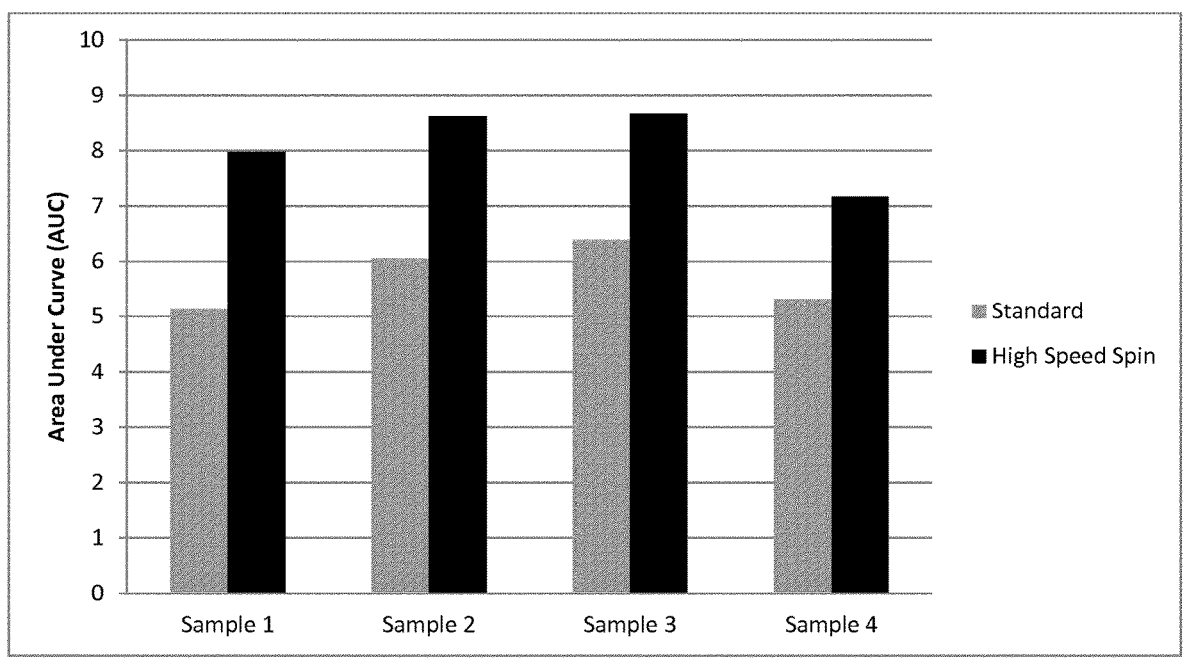
Figure 6:
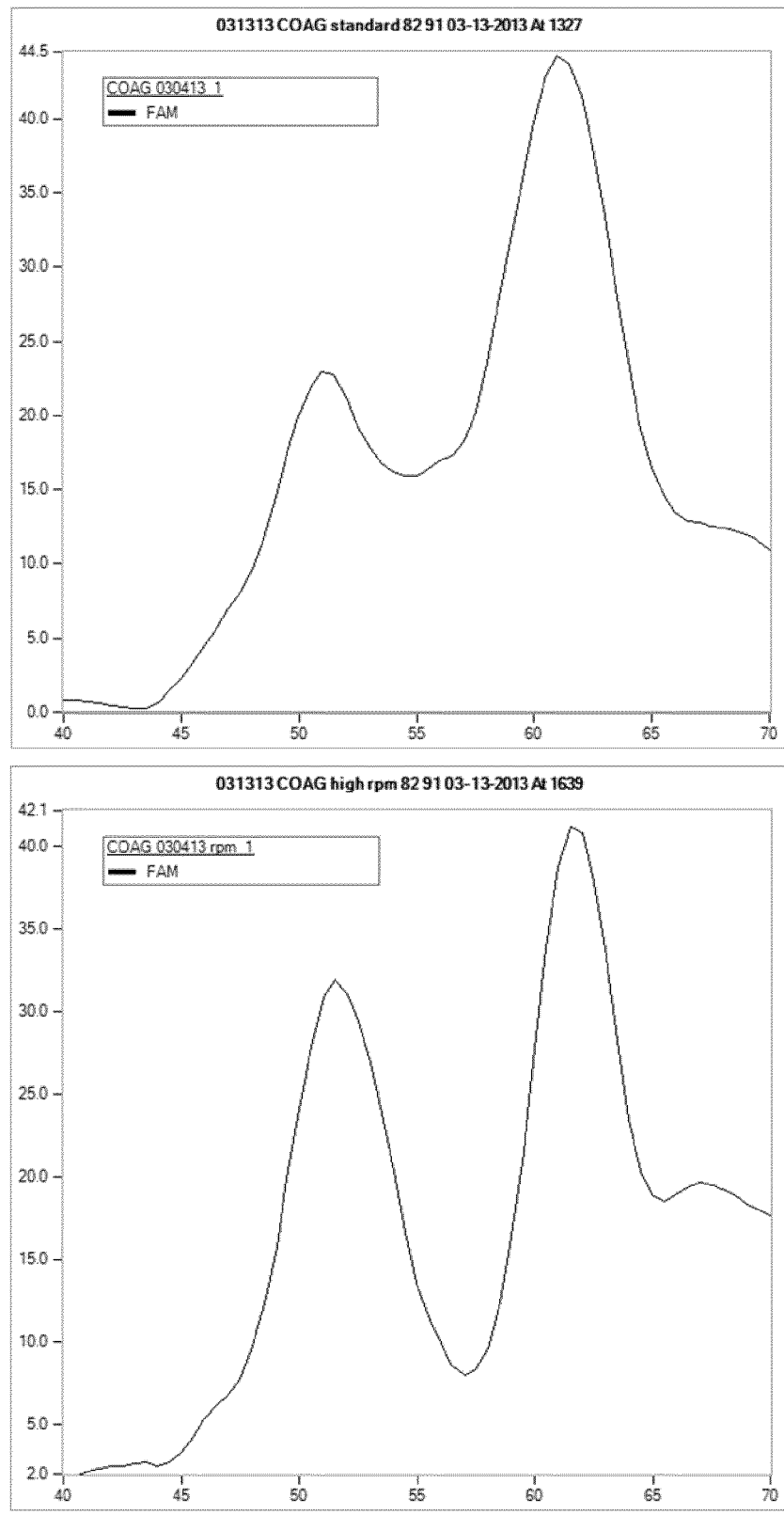

*Bacillus anthracis* was diluted in whole blood. The identical samples were run with an assay definition that spun the samples for six minutes at 780×g at the beginning of the run (slower spin) versus another assay definition which spun the samples at about 5000 rpm (1500×g) for two minutes at the beginning of the run (high speed spin). In both cases, samples were spun at the standard speed of about 1500 rpm (about 140×g) for the remainder of the run. The effects of initial rotational speed on optimizing the fluorescence intensity and Ct values for *Bacillus anthracis* detection are shown in FIG. 3.

C. Viral Hemorrhagic Fever Panel

Inactivated Ebola Reston virus was diluted in whole blood or PBS buffer. The identical samples were run using reagents that were able to detect Ebola virus and Marburg virus, and differentiate Ebola Reston and Ebola Zaire viruses. Results were compared to an assay definition that spun the samples at about 1500 rpm (about 140×g) during the whole assay, which is the standard methodology, and another assay definition which spun the samples at about 5000 rpm (1500×g) for the whole assay except during the optical reading step, when the samples were spun at the standard speed of about 1500 rpm (about 140×g). The amplification profiles from use of high rotational speed at 5000 rpm to detect a viral hemorrhagic fever from the virus Ebola Reston are shown in FIG. 4.

The results presented above demonstrate successful amplification and detection of a nucleic acid directly from whole blood of *Bacillus anthracis*, the Viral Hemorrhagic Fever panel and the Dengue fever serotypes.

Example 3

Effect of Universal Disc High Speed Spin on Amplification and Melt Analysis of Human DNA in Whole Blood Molecular tests for mutations in genes responsible for coagulation related to thrombosis such as Factor V, Factor II and MTHFR genes were performed to determine the effect of high speed spin on detection and amplification of human DNA in whole blood.

Two identical Universal Discs were prepared with reaction mixes including primers and Hybeacon™ probes for single nucleotide polymorphisms in the methylenetetrahydrofolate reductase (MTHFR) gene. The reaction consisted of 8 μL of reaction mix plus 2 μL of whole blood or buffer as the sample or 9 μL of reaction mix plus 1 μL of whole blood or buffer. Two discs were run using separate parameters: one with the standard PCR followed by melt analysis protocol, and the other with the standard protocol but a high speed spin step added between the PCR cycles and the melt analysis step. The results, shown in FIG. 5, demonstrate that the high speed spin increased the area under the melt curve values for the majority of the blood samples, thus increasing the difference between the positive and no template samples. In a similar experiment looking at the detection of MTHFR 1298 heterozygote from whole blood patient specimen, introduction of a high spin resulted in sharp peak differentiation for heterozygote determination as compared to standard speed (FIG. 6.)

These results demonstrate improved detection and amplification of nucleic acids of any microorganisms, including but not limited to, bacteria, viruses and fungi, as well as human nucleic acids, in whole blood. These results also show that centrifugation of whole blood samples at high speed reduces background fluorescence, eliminates cellular debris, such as lysed and intact red blood cells, and fluorescence interference and quenching, and prevents undesirable amplification curve variations which can cause false reading and/or mask amplification curves.

The contents of the articles, patents, and patent applications, and all other documents and electronically available information mentioned or cited herein, are hereby incorporated by reference in their entirety to the same extent as if each individual publication was specifically and individually indicated to be incorporated by reference. Applicants reserve the right to physically incorporate into this application any and all materials and information from any such articles, patents, patent applications, or other physical and electronic documents.

The invention illustratively described herein may suitably be practiced in the absence of any element or elements, limitation or limitations, not specifically disclosed herein. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the inventions embodied therein herein disclosed may be resorted to by those skilled in the art, and that such modifications and variations are considered to be within the scope of this invention.

The invention has been described broadly and generically herein. Each of the narrower species and subgeneric groupings falling within the generic disclosure also form part of the invention. This includes the generic description of the invention with a proviso or negative limitation removing any subject matter from the genus, regardless of whether or not the excised material is specifically recited herein. Other embodiments are within the following claims. In addition, where features or aspects of the invention are described in terms of Markush groups, those skilled in the art will recognize that the invention is also thereby described in terms of any individual member or subgroup of members of the Markush group.

The invention claimed is:

1. A method for identifying the presence or absence of a target nucleic acid in a biological sample, the method comprising:

(a) directly amplifying and detecting a target nucleic acid in a biological sample containing whole blood using a real-time polymerase chain reaction (PCR) assay, wherein the target nucleic acid is not extracted from the biological sample prior to amplifying; and (b) rotating a biological sample during one or more steps of the real-time PCR assay at a rotational velocity of greater than 140×g and less than or about 1500×g, wherein the rotational velocity is sufficient to pellet cellular debris and fluorescence inhibitors present within the sample to reduce fluorescence interference or quenching in the sample.

2. The method of 1 claim, wherein the biological sample is placed in a microfluidic disc capable of being subjected to centrifugal force.

3. The method of claim 1, wherein the detecting step comprises detecting a visible signal emitted through an optical path in the rotated sample.

4. The method of claim 1, wherein the detectable signal is a fluorescent emission.

5. The method of claim 1, wherein the target nucleic acid is DNA.

6. The method of claim 1, wherein the target nucleic acid is RNA.

7. The method of claim 1, wherein the target nucleic acid is from one or more organisms found in blood.

8. The method of claim 7, wherein the target nucleic acid is a human nucleic acid.

9. The method of claim 7, wherein the target nucleic acid is from a microorganism.

10. The method of claim 9, wherein the microorganism is a virus.

11. The method of claim 10, wherein the virus is one or more of an Ebola virus, Marburg virus, an influenza virus, a respiratory syncytial virus, a varicella zoster virus, a herpes simplex virus, an enterovirus, a Dengue virus, or any combination thereof.

12. The method of claim 9, wherein the microorganism is a bacterium.

13. The method of claim 12, wherein the bacterium is a gram-negative or a gram-positive bacterium.

14. The method of claim 13, wherein the bacterium is one or more of *Bacillus, Bordetella, Borrelia, Listeria, Escherichia, Salmonella, Campylobacter, Clostridium, Helicobacter, Mycobacterium, Staphylococcus, Campylobacter, Enterococcus, Neisseria, Shigella, Streptococcus, Vibrio, Yersinia*, and *Pseudomonas*, or any combination thereof.

15. The method of claim 14, wherein the bacterium is *Bacillus anthracis*.

16. The method of claim 9, wherein the microorganism is a fungus.

17. The method of claim 1, wherein cellular debris comprises lysed and intact red blood cells and denatured proteins that can physically block or quench fluorescence.

18. The method of claim 1, wherein the biological sample is rotated at a rotational velocity of about 1500×g.

* * * * *